(12) United States Patent
Duong et al.

(10) Patent No.: US 7,640,116 B2
(45) Date of Patent: Dec. 29, 2009

(54) METHOD FOR DETECTION OF SELECTED CHEMICALS IN AN OPEN ENVIRONMENT

(75) Inventors: Tuan Duong, Glendora, CA (US); Margaret Ryan, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/518,535

(22) Filed: Sep. 7, 2006

(65) Prior Publication Data

US 2008/0065334 A1    Mar. 13, 2008

Related U.S. Application Data

(60) Provisional application No. 60/715,353, filed on Sep. 7, 2005.

(51) Int. Cl.
    *G01N 33/00* (2006.01)
(52) U.S. Cl. ............................. 702/22; 702/27; 702/30; 702/32
(58) Field of Classification Search ............... 702/22, 702/23, 24, 27, 30, 32
    See application file for complete search history.

(56) References Cited

U.S. PATENT DOCUMENTS

| | | | |
|---|---|---|---|
| 6,411,905 B1 * | 6/2002 | Guoliang et al. ............... | 702/23 |
| 6,944,571 B2 * | 9/2005 | Hahn et al. .................. | 702/179 |
| 2002/0052694 A1 * | 5/2002 | McGregor et al. ............ | 702/19 |
| 2003/0046038 A1 * | 3/2003 | Deligne et al. .............. | 702/190 |
| 2003/0088384 A1 * | 5/2003 | Hori et al. ................... | 702/189 |
| 2005/0032231 A1 * | 2/2005 | Smaragdis .................. | 436/139 |
| 2005/0208673 A1 * | 9/2005 | Labreche et al. ............ | 436/149 |
| 2006/0200318 A1 * | 9/2006 | Morishita et al. ............. | 702/20 |
| 2007/0192035 A1 * | 8/2007 | Schweitzer et al. ........... | 702/19 |
| 2008/0234948 A1 * | 9/2008 | Walk et al. .................... | 702/23 |

OTHER PUBLICATIONS

Kermit et al., "Independent component analysis applied on gas sensor array measurement data", IEEE Sensors Journal, vol. 3, Issue 2, Apr. 2003 pp. 218-228.*
Chen et al., "Improving the classification accuracy in electronic noses using multi-dimensional combining (MDC)", Proceedings of IEEE Sensors, vol. 2, Oct. 24-27, 2004 pp. 587-590.*

(Continued)

*Primary Examiner*—Jeffrey R West
(74) *Attorney, Agent, or Firm*—Tope-McKay & Associates

(57) ABSTRACT

The present invention relates to a space-invariant independent component analysis and electronic nose for detection of selective chemicals in an unknown environment, and more specifically, an approach to analysis of sensor responses to mixtures of unknown chemicals by an electronic nose in an open and changing environment. It is intended to fill the gap between an alarm, which has little or no ability to distinguish among chemical compounds causing a response, and an analytical instrument, which can distinguish all compounds present but with no real-time or continuous event monitoring ability.

1 Claim, 15 Drawing Sheets

OTHER PUBLICATIONS

Chen et al., "Multi-Dimension Combining (MDC) in abstract Level and Hierarchical MDC (HMDC) to Improve the Classification Accuracy of Enoses", Proceedings of the IEEE Instrumentation and Measurement Technology Conference, vol. 1, May 16-19, 2005, pp. 683-686.*

Natale et al., "Counteraction of environmental disturbances of electronic nose data by independent component analysis", Sensors and Actuators B: Chemical, vol. 82, No. 2, Feb. 28, 2002, abstract.*

Ryan, M.A., at al., "Monitoring the air quality in a closed chamber using an electronic nose," Proceedings of the 27th International Conference on Environmental Systems, Society of Automotive Engineers 1997, 97-ES84.

Ryan, M.A., et al., "Monitoring space shuttle air for selected contaminants using an electronic nose," Proceedings of the 28th International Conference on Environmental Systems, Society of Automotive Engineers 1998, 98156.

Ryan, M.A., et al., "Operation of an electronic nose aboard the space shuttle and directions for research for a second generation device," Proceedings of the 30th International Conference on Environmental Systems, Society of Automotive Engineers 2000, 00ICES-295.

Spacecraft Maximum Allowable Concentrations for Selected Airborne Contaminants, National Academy Press: Washington, DC, 1994; vols. 1 & 2.

Fahlman, S.E., et al., "The cascade correlation learning architecture," in Advances in Neural Information Processing Systems II, Ed: D. Touretzky, Morgan Kaufmann, San Mateo, CA, pp. 524-532.

T.A. Duong, et al., "Convergence analysis of cascade error projection: an efficient hardware learning algorithm," International Journal of Neural System, vol. 10, No. 3, pp. 199-210, Jun. 2000.

J. Herault, et al., "Space or time adaptive signal processing by neural network models," In Denker J. S. (ed), editor, Neural network for computing: AIP Conference proceedings 151, New York. American Institute for Physics, 1986.

C. Jutten, et al., "Blind separation of the sources, part I: an adaptive algorithm based on neuromimetic architecture," Signal Processing, 24: 1-10, 1991.

P. Common, "Independent component analysis—a new concept?" Signal Processing, 36(3): 287-314, 1994.

D-T. Pham, et al., "Blind Separation of a mixtures of independent sources through a maximum likelihood approach," In EUSIPCO pp. 771-774, 1992.

J. Cardoso, "High-order contrast for independent component analysis," Neural Computation 1998(a).

A.J. Bell, et al., "An information-maximization approach to blind separation and blind deconvolution," Neural Computation, 7: 1129-1159, 1995.

S.I. Amari, "Natural gradient works efficiently in learning," Neural Computation, 1998.

James, J.T., et al., "Volatile organic contaminants found in the habitable environment of the space shuttle," STS-26 to STS-55, Aviation Space Environ. Med. 1994, 65, 851-857.

* cited by examiner

Spacecraft Maximum Allowable Concentrations (SMAC) in PPM

| Target Compound | Concentration Range Tested (ppm) | 1 hr. SMAC (ppm) | Reference Number |
|---|---|---|---|
| Benzene | 10 – 50 | 30 | 1 |
| Ethanol | 10 – 130 | 2000 | 2 |
| Freon | 50 – 525 | 50 | 3 |
| Indole | 006 – 0.06 | 1 | 4 |
| Methane | 3000 – 7000 | 5300 | 5 |
| Methanol | 10 – 300 | 30 | 6 |
| Propanol | 75 – 180 | 400 | 7 |
| Toluene | 30 – 60 | 16 | 8 |
| Ammonia | 10 – 50 | 30 | 9 |
| Formaldehyde | 50 – 510 | 0.4 | 10 |
| Medical Wipe | 500 – 4000 | N/A | 13 |

FIG. 1

Fig. 2 a) a JPL ENose sensor substrate on the left with eight polymer-carbon composite sensors, b) the complete JPL ENose on the right.

Table Depicting Four Data Sets Used to Identify Chemicals Within Chemical Mixtures

| Data set | Number of variables (sensors) | Mixture of chemical nos. | Number of samples available |
|---|---|---|---|
| 1 | 16 | 1 & 7 | 12 |
| 2 | 16 | 3 & 10 | 9 |
| 3 | 16 | 2 & 13 | 8 |
| 4 | 16 | 2 & 5 | 8 |

FIG. 6

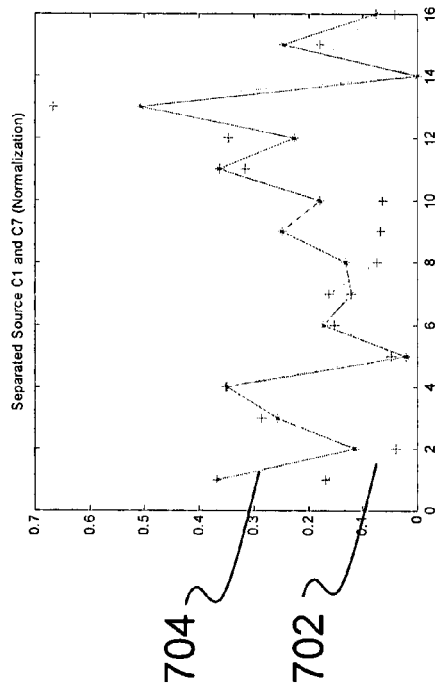
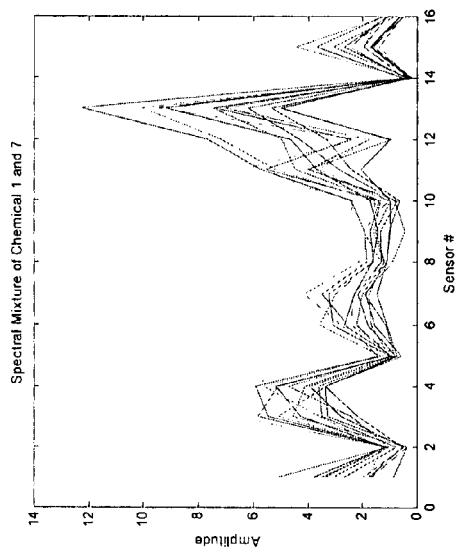
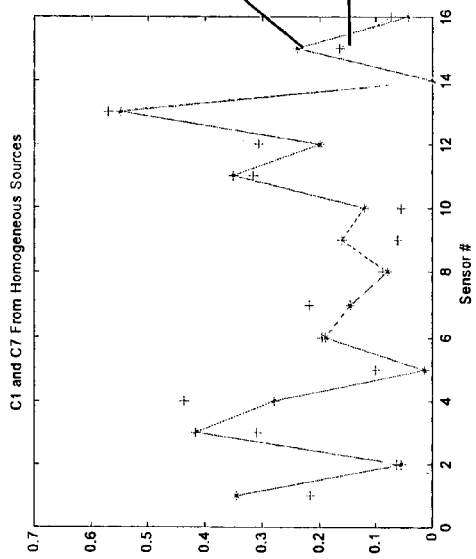
FIG. 7B
FIG. 7A
FIG. 7C

Separated Sources Chemicals 1 & 7 Projected On The 11 Known Chemicals By ICA (Bold entries show greatest overlap for that chemical)

| Single chemical source (ref. #) | Separated chemical 1 | Separated chemical 7 |
|---|---|---|
| 1 | 0.8457 | 0.9601 |
| 2 | 0.4772 | 0.6291 |
| 3 | 0.7325 | 0.9369 |
| 4 | 0.6286 | 0.5258 |
| 5 | 0.7433 | 0.6996 |
| 6 | 0.4872 | 0.4304 |
| 7 | 0.7944 | 0.9876 |
| 8 | 0.7938 | 0.9014 |
| 9 | 0.6679 | 0.5737 |
| 10 | 0.5271 | 0.6051 |
| 13 | 0.6223 | 0.7896 |

FIG. 8

Correlation Between The original And Separated Sources of Chemicals 3 & 10 (Bold entries indicate source chemical with highest correlation)

| Single chemical source (ref. #) | Separated chemical 3 | Separated chemical 10 |
|---|---|---|
| 1 | 0.8250 | 0.7723 |
| 2 | 0.4760 | 0.8282 |
| 3 | 0.9464 | 0.8254 |
| 4 | 0.5235 | 0.4420 |
| 5 | 0.6134 | 0.8935 |
| 6 | 0.3414 | 0.7670 |
| 7 | 0.8681 | 0.7829 |
| 8 | 0.8165 | 0.8887 |
| 9 | 0.6561 | 0.7803 |
| 10 | 0.6125 | 0.9619 |
| 13 | 0.7200 | 0.9444 |

FIG. 10

Correlation Between The Original And Separated Sources of Chemicals 2 & 13 (Bold entries indicate source chemical with highest correlation)

| Single chemical source (ref. #) | Separated chemical 2 | Separated chemical 13 |
|---|---|---|
| 1 | 0.6194 | 0.6916 |
| 2 | 0.9893 | 0.9225 |
| 3 | 0.5733 | 0.6970 |
| 4 | 0.3166 | 0.3574 |
| 5 | 0.7677 | 0.9007 |
| 6 | 0.8016 | 0.8116 |
| 7 | 0.7037 | 0.7350 |
| 8 | 0.7643 | 0.8269 |
| 9 | 0.5654 | 0.7117 |
| 10 | 0.8331 | 0.9598 |
| 13 | 0.9257 | 0.9709 |

FIG. 12

Correlation Between The Original And Separated Sources of Chemicals 2 & 5 (Bold entries indicate source chemical with highest correlation)

| Single chemical source (ref. #) | Separated chemical 2 | Separated chemical 5 |
|---|---|---|
| 1 | 0.7311 | 0.8138 |
| 2 | 0.9017 | 0.7261 |
| 3 | 0.6623 | 0.7240 |
| 4 | 0.3824 | 0.5042 |
| 5 | 0.8992 | 0.8639 |
| 6 | 0.7301 | 0.6039 |
| 7 | 0.7450 | 0.7974 |
| 8 | 0.8098 | 0.8247 |
| 9 | 0.6086 | 0.6377 |
| 10 | 0.8753 | 0.7447 |
| 13 | 0.8680 | 0.7566 |

FIG. 14

Projection Mean & Standard Deviation for Chemicals 1 & 7 for each Source Clearly Identify Proper Source (Bold entries indicate highest correlation)

| Single chemical source (ref.#) | Mean Separated chemical 7 | Standard deviation | Mean Separated chemical 1 | Standard deviation |
|---|---|---|---|---|
| 1 | 0.8851 | 0.0830 | 0.8959 | 0.0890 |
| 2 | 0.5893 | 0.1405 | 0.5551 | 0.0792 |
| 3 | 0.8728 | 0.0784 | 0.8046 | 0.0397 |
| 4 | 0.4973 | 0.0723 | 0.5057 | 0.1541 |
| 5 | 0.6611 | 0.0599 | 0.7285 | 0.0742 |
| 6 | 0.4161 | 0.0970 | 0.4465 | 0.0903 |
| 7 | 0.9222 | 0.0765 | 0.8664 | 0.1104 |
| 8 | 0.8398 | 0.0604 | 0.8141 | 0.1099 |
| 9 | 0.5539 | 0.0460 | 0.5601 | 0.1031 |
| 10 | 0.5671 | 0.1103 | 0.5702 | 0.1141 |
| 13 | 0.7342 | 0.1096 | 0.6902 | 0.1101 |

FIG. 15

METHOD FOR DETECTION OF SELECTED CHEMICALS IN AN OPEN ENVIRONMENT

PRIORITY CLAIM

The present application is a non-provisional utility application, claiming benefit of priority of U.S. Provisional Patent Application No. 60/715,353, filed Sep. 7, 2005, titled "Smart Enose for Chemical Detection in the Open Environment."

STATEMENT OF GOVERNMENT INTEREST

The invention described herein was made in the performance of work under a NASA contract and is subject to the provisions of Public Law 96-517 (35 USC 202) in which the Contractor has elected to retain title.

BACKGROUND OF THE INVENTION (1) Technical Field

The present invention relates to a space-invariant independent component analysis and electronic nose for detection of selective chemicals in an unknown environment, and more specifically to an approach to analysis of sensor responses to mixtures of unknown chemicals by an electronic nose in an open and changing environment.

(2) Background

The need for low-power, miniature sensor devices that can monitor air quality in an enclosed space with multi-compound capability and minimum human operation led to the development of a polymer-carbon composite based electronic nose (ENose) at NASA's Jet Propulsion Laboratory (JPL). The sensor array in the JPL ENose consists of 32 conductometric sensors made from insulating polymer films loaded with carbon. In its current design, it has the capability to detect 10 common contaminants which may be released into the recirculated breathing air of a space shuttle or space station released from a spill or a leak; target concentrations are based on the 1-hour Spacecraft Maximum Allowable Concentrations (SMAC) set by NASA, depicted in FIG. 1, and are in the parts-per-million (ppm) range. The ENose was intended to fill the gap between an alarm, which has little or no ability to distinguish among chemical compounds causing a response, and an analytical instrument, which can distinguish all compounds present but with no real-time or continuous event monitoring ability.

As in other array-based sensor devices, the individual sensor films of the ENose are not specific to any one analyte; it is in the use of an array of different sensor films that gases or gas mixtures can be uniquely identified by the pattern of measured response. The response pattern requires software analysis to deconvolute gas compounds and their concentrations.

An example sensor set is shown on the left in FIG. 2, with the complete assembled device shown on the right.

What is needed is a method of detection for selective chemicals as a result of leaks or spills of specific compounds. It has been shown in analysis of samples taken from space shuttle flights that, in general, air is kept clean by the air revitalization system and contaminants are present at levels significantly lower than the SMACs; the ENose has been developed to detect target compounds released suddenly into the breathing environment. A leak or a spill of a solvent or other compound would be an unusual event.

What is needed is an approach to analysis of sensor responses to mixtures of chemical compounds so that use of the ENose may by extended to detect chemical compounds in an open and changing environment, such as a building or a geographical area where air exchange is not controlled and limited. In an open environment, the collected sensory data will be comprised of a mixing between unknown chemicals with unknown mixing levels (coefficient) between them. The identification of chemical compounds among these mixing chemicals is a challenge for real world applications.

To determine whether a chemical compound exists in the an environment, one of the most well-known techniques is to recover the original chemicals. When done, the detection can be an easy step by determining the minimum phase between the predicted original reactants and the target chemicals. A more sophisticated method is to use a neural network approach, which can be employed to capture the target chemicals in various conditions, e.g., concentration levels through the parameterized weight set. Then, the strongest correlation between parameterized weight and the predicted original can be used to identify the intended chemical.

Recently, Independent Component Analysis (ICA) has proven effective to not only de-correlate second order statistics of the signals but also reduce higher order statistical dependencies. ICA transforms an observed signal vector into a set of signals that are as statistically independent as possible. Theoretically, ICA is an information-theoretic approach, which exploits concepts from information theory such as entropy and mutual information.

The ICA roots in the early work of Herault and Jutten who first introduced an adaptive algorithm in a simple feedback architecture that was able to separate several unknown independent sources. ICA was further developed, and recent improvements used natural gradient descent based on the Riemannian metric tensor to optimize the curvature of a particular manifold in n dimensional space. This technique is employed to apply to the Infomax to simplify the learning rule used here. ICA has applications for feature extraction in speech recognition systems, in communication systems, in medical signal processing, and in image processing.

Therefore, what is needed is an ICA method for detection of selective chemicals in an unknown environment using an electronic nose.

SUMMARY OF THE INVENTION

The present invention relates to a space-invariant independent component analysis and electronic nose for detection of selective chemicals in an unknown environment, and more specifically, to an approach to analysis of sensor responses to mixtures of unknown chemicals by an electronic nose in an open and changing environment.

In one aspect of the present invention, a method for detection of chemicals in an open environment comprises the acts of obtaining sampled data by sampling data from a database containing air samples of an unknown open environment; utilizing an electronic nose sensor array containing a plurality of sensors evaluating the sampled air over a plurality of time intervals; partitioning the sampled data with respect to each time interval into a subset; sampling a subset of the sampled data with respect to time for each sensor; calculating operating points of the subset of the sampled data as the averaged value (e.g., mean value) of the subset of the sampled data; linearizing the subset of the sampled data using the operating points; determining a data distribution corresponding to the linearized subset of the sampled data; performing an independent component analysis (ICA) on the linearized subset of the sampled data by using the data distribution, wherein the ICA generates independent component vectors (recovered sources) representing the subset of the sampled data; sampling known chemical elements representing spectral vectors from a database; iteratively performing an act of projecting the independent component vectors (recovered source) representative of the subset of the sampled data onto the independent component vectors of the known chemical elements, wherein the step of projecting further comprises the steps of: finding a correlation between the independent component vector of a subset of the sampled data and the spectral vectors of the known chemical elements; finding a maximum correlation point on the correlation and a known chemical element corresponding to the maximum correlation point; creating a list of chemical elements detected on the subset of the sampled data, wherein a known chemical element corresponding to the maximum correlation point is added to the list of chemical elements detected; outputting the list of chemical elements detected on the subset of the sampled data.

BRIEF DESCRIPTION OF THE DRAWINGS

The objects, features and advantages of the present invention will be apparent from the following detailed descriptions of the disclosed aspects of the invention in conjunction with reference to the following drawings, where:

FIG. 1 is a table depicting the 1-hour Spacecraft Maximum Allowable Concentrations (SMAC) of chemicals as determined by NASA;

FIG. 6 is a table depicting the four sets of data used to detect selective chemicals from chemical mixtures;

FIG. 7A is a graphical representation of twelve mixtures of chemicals 1 and 7 used in Experiment 1;

FIG. 7B is a graphical representation of separated signal sources of chemicals 1 and 7 by space-invariant ICA of twelve inputs;

FIG. 7C is a graphical representation of the average of the single chemical source 1 and 7;

FIG. 8 is a table depicting a projection of the separated chemical sources 1 and 7 on the original chemical;

FIG. 10 is a table depicting a projection of the separated chemical sources 3 and 10 on the original chemical;

FIG. 12 is a table depicting a projection of the separated chemical sources 2 and 5 on the original chemical;

FIG. 14 is a table depicting a projection of the separated chemical sources 2 and 5 on the original chemical; and FIG. 15 is a table depicting the mean and standard deviation of its projection of separated sources of chemical 1 and chemical 7 on each single chemical source, demonstrating the successful identification of the separated chemical sources.

DETAILED DESCRIPTION

Figure 2:
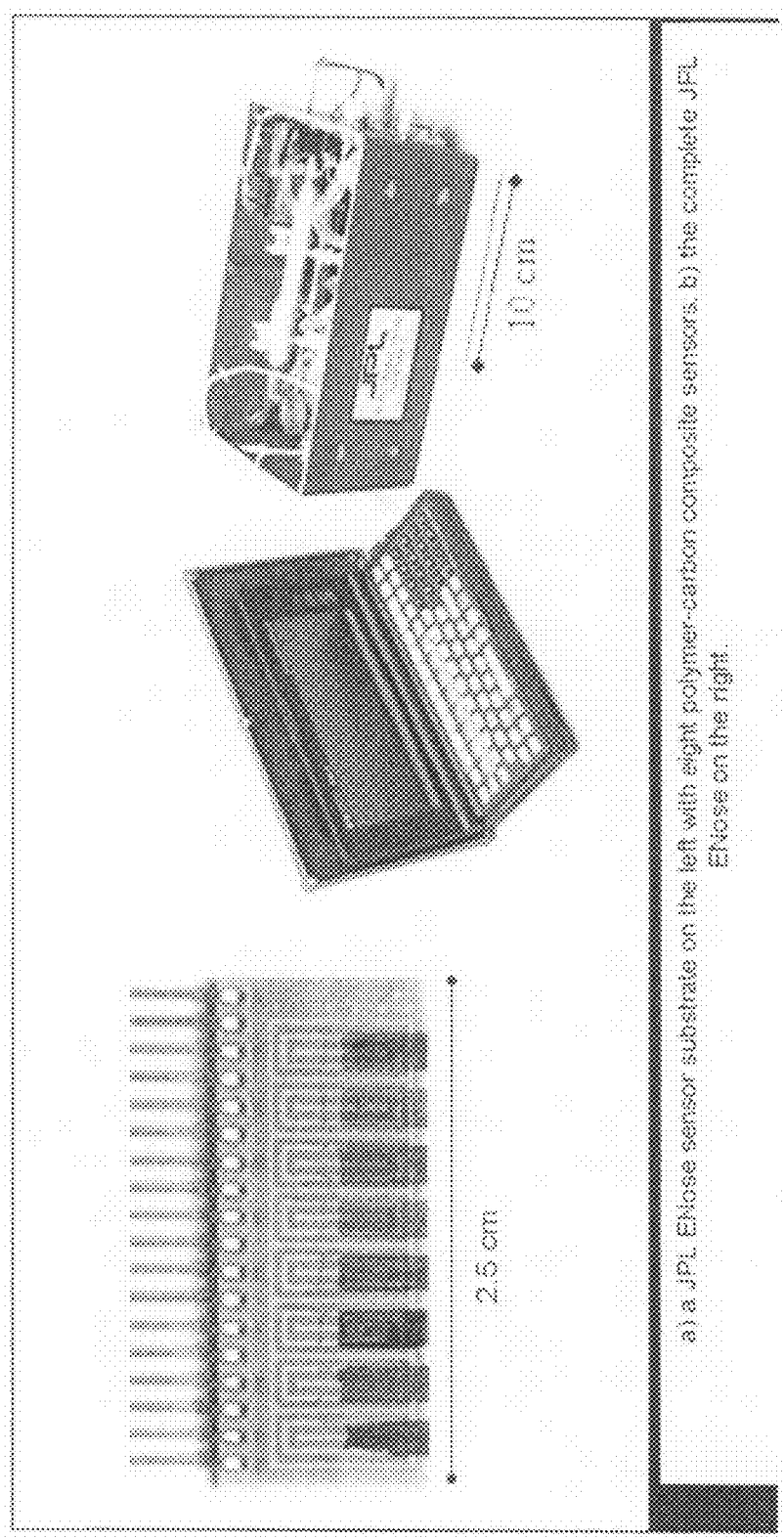
FIG. 2 is a photograph of a sensor set of an electronic nose (Enose) and assembled Enose device.
Figure 3:
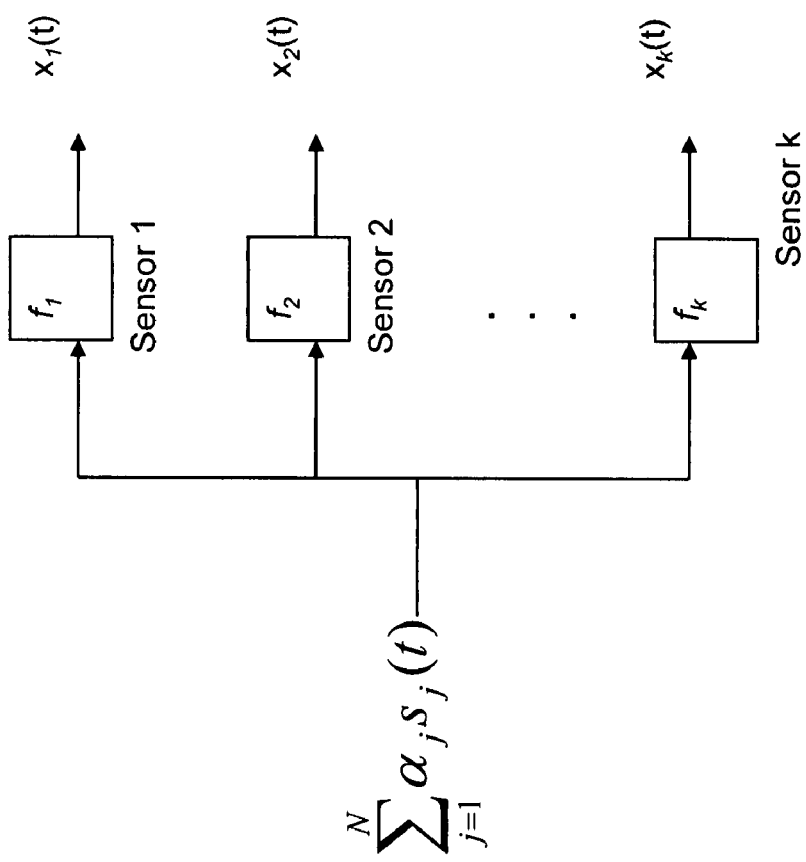
FIG. 3 is a diagram of the system model and setup topology of an Enose array.

The present invention relates to a space-invariant independent component analysis and electronic nose for detection of selective chemicals in an unknown environment, and more specifically, to an approach to analysis of sensor responses to mixtures of unknown chemicals by an electronic nose in an open and changing environment.

The following description, taken in conjunction with the referenced drawings, is presented to enable one of ordinary skill in the art to make and use the invention and to incorporate it in the context of particular applications. Various modifications, as well as a variety of uses in different applications, will be readily apparent to those skilled in the art, and the general principles, defined herein, may be applied to a wide range of embodiments. Thus, the present invention is not intended to be limited to the embodiments presented, but is to be accorded the widest scope consistent with the principles and novel features disclosed herein. Furthermore, it should be noted that unless explicitly stated otherwise, the figures included herein are illustrated diagrammatically and without any specific scale, as they are provided as qualitative illustrations of the concept of the present invention.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents that are filed concurrently with this specification and are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

The present invention provides a space-invariant topology to enable an Independent Component Analysis (ICA) to solve chemical detection from two unknown mixing chemical sources. The specific system architecture enables the space-invariant ICA to achieve a robust independent signal source separation in an unknown open environment. Additionally, the system architecture provides an optimal topology for hardware-friendly implementation and an effective architecture for reduced data source requirements.

The space-invariant topology along with the techniques of maximum entropy information and natural gradient descent demonstrates that it is effective to separate the two mixed unknown chemical sources with unknown mixing levels to the array of two original sources under insufficient sampled data. From separated sources, they can be identified by projecting them on 11 known chemical sources to find the best match for detection.

Simulations have shown that 100% correct detection could be achieved under two cases: a) under-completed case where the number of input mixtures is larger than number of original chemical sources; and b) regular case where the number of input mixtures is the same as the number of original chemical sources. The time-invariant topology approach may face obstacles with an over-complete case, insufficient data and cumbersome topology.

Four sets of unknown paired mixture sources are collected via an electronic nose, which, in one non-limiting example, is a JPL 16-ENose sensor array (made at the Jet Propulsion Laboratory, Pasadena, Calif.). The Enose collects the mixture sources in the unknown environment with, at most, 12 samples' data collected. Per time-invariant aspect, this appears to be an over-complete case in ICA where the number of outputs (32) is larger than the number of inputs (16).

Technical Approach

In one non-limiting example, the approximation of the set up topology of the electronic nose array is shown in FIG. 1. The collected sensing data $x_i(t)$ consists of changes in electrical resistance corresponding to sensor response to the unknown mixture of chemical sources $s_i$ and their densities (or concentrations) at the time t.

Due to the small separation between the sensors themselves, the input of each sensor resistance is assumed to be uniquely distributed. The sensory data can be modeled as follows:

$$x_i(t) = f_i\left(\sum_{j=1}^{N} \alpha_j s_j(t)\right) \quad i = \overline{1-k} \quad (1)$$

Where $f_i$ is the unknown non-linear activation, $\alpha_j$ is the unknown mixing coefficient of chemical source j, and i is the index of sensor number and N as number of sensor and $s_j$ is original source.

From equation (1), using the first order of a Taylor expansion, it is rewritten:

$$x_i = a_i + \sum_{j=1}^{N} \beta_{ij} s_j \quad (2)$$

$$\text{Where } a_i = f_i\left(\sum_{j=1}^{N} \alpha_j s_j^o\right) + \sum_{j=1}^{N} \left.\frac{\partial f_i}{\partial s_i}\right|_{s_j^o} \alpha_j s_j^o$$

$$\text{and } \beta_{ij} = \left.\frac{\partial f_i}{\partial s_j}\right|_{s_j^o} \alpha_j \quad (3)$$

And $s_j^o$ is an operating point of the source $s_j$. For each sampling data point in time for the same sensor i, $x_i$ fluctuates around its operating point $\alpha_i$ and it can be considered as a common bias for $x_i(t)$ with $t\epsilon[t, t+k\Delta t]$. From this argument, Equation (2) can be simplified to:

$$Y = \begin{bmatrix} x_1 - a_1 \\ x_2 - a_2 \\ \ldots \\ x_k - a_k \end{bmatrix}$$

$$Y = \Gamma S$$

Where Y is unbiased mixture data, $\Gamma$ is the unknown mixing matrix and S is the chemical source signal.

The learning rule based on the maximum entropy algorithm is given by:

$$y=g(u)=g(Wx); \quad (5)$$

where g is a non linear function e.g the logistic function or hyperbolic tangent function. The update weight can be calculated as:

$$\Delta W = W^{-T} + \Phi(u)x^T; \quad (6)$$

where $W^{-T}$ is an inverse transport of the NXN weight matrix W, $x^T$ is a mixing input vector (observed vector), and $$\Phi(u) = [\phi_i(u_i)] = \left[\frac{\partial y_i'}{\partial y_i}\right]. \quad (7)$$

To simplify equation (5) using a natural gradient descent technique, the learning rule can be:

$$\Delta W = (I + \Phi(u)u^T)W \quad (8)$$

With u=Wx

Space-Invariant Architecture

The most common ICA approach is that the number of variables and the number of sources are the same. However, in this study there are two obstacles: 1) there are 12 or less samples (mixing chemical compounds) from each sensor and the total number of sensor is 16 and they do not have sufficient data set (at least 16 data samples required); and 2) the number of variables is 16 as number of sensors while the number of compounds in a mixture is 2 and it is considered over complete case.

Figure 4:
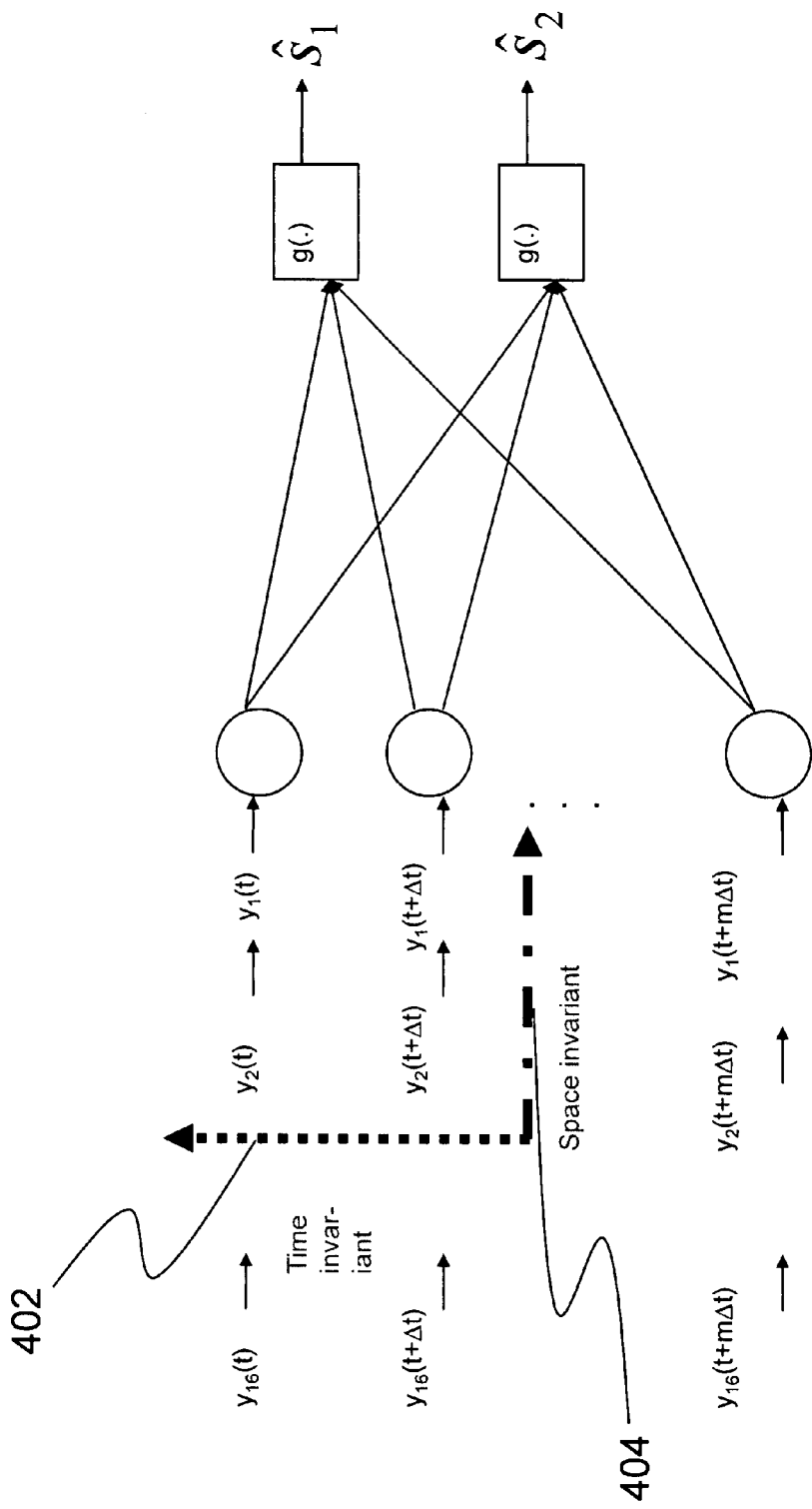
FIG. 4 is a diagram depicting the difference between a time-invariant independent component analysis (ICA) of the prior art and the space-invariant ICA architecture of the present invention.

For the time-invariant approach, the data that will flow orthogonal 402 with the time-invariant direction as shown in FIG. 4 and will require 32 outputs (16 channels for each chemical compound). The topology is 16 inputs, 32 outputs and 12 or less sample data which may not be a solvable problem.

Instead of using a time-invariant approach, the space-invariant approach 404 allows for more data points and enables the square mapping matrix (the dimension of mixing sources and sensors are the same). This approach is feasible due to the mathematical model based on equations (2)-(4). The architectures are shown in FIG. 4. In FIG. 4, the unbiased input $Y_i(t)$ (i=1-k) is based on temporal mixture data and the sensory data are spatially invariant.

Figure 5:
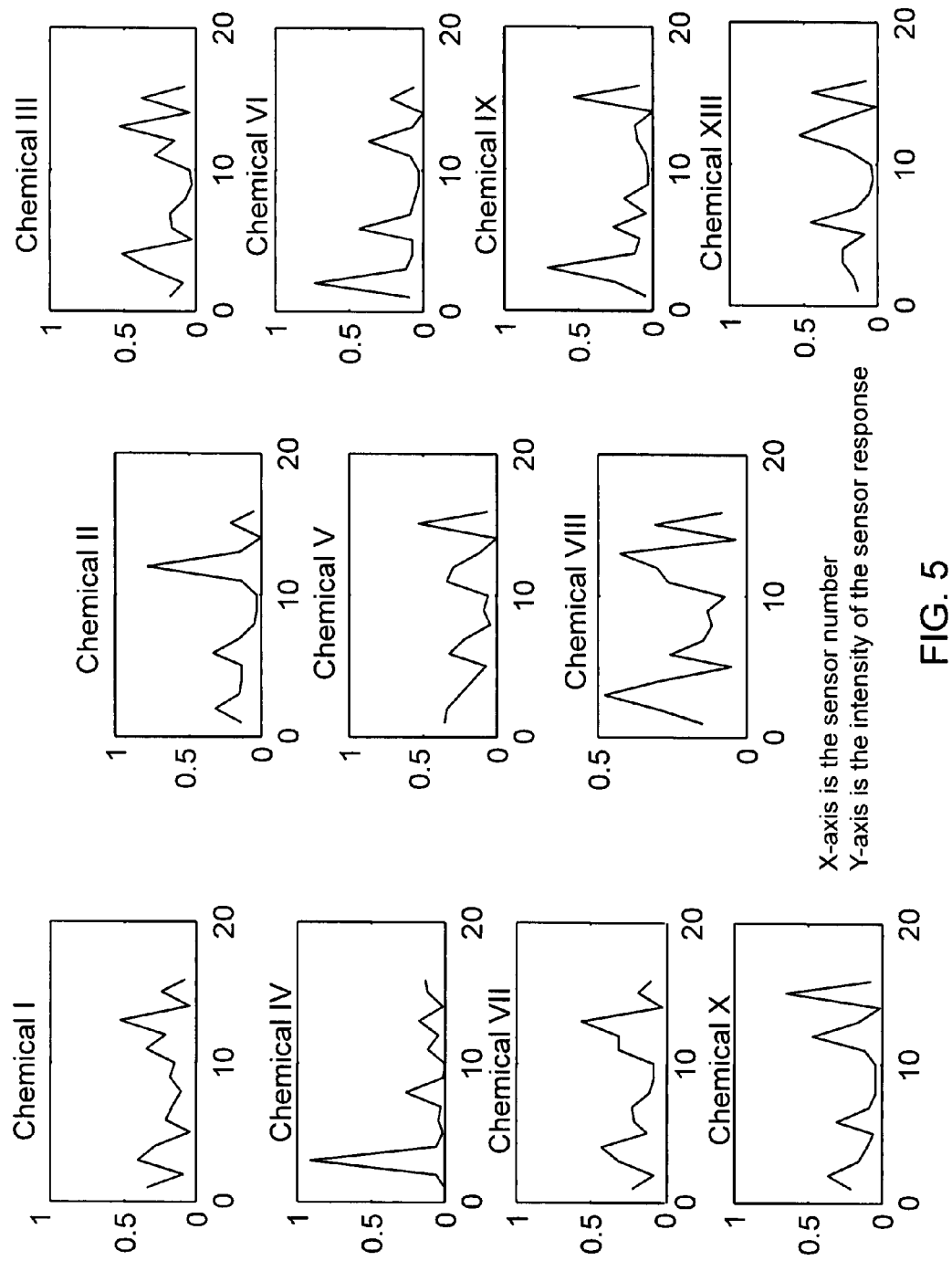
FIG. 5 is a graphical illustration of the spectra of eleven chemicals used for comparison with mixtures of chemicals from an unknown source.

From laboratory set up, a set of single spectra of 11 chemicals using 16 elements is collected in the ENose sensor array; it is averaged and shown in FIG. 5. A database may also contain the sampled data of air samples from an unknown environment to be used in the calculations.

In this embodiment, the number of sensors used is 16 and mixing chemical sources is 2; four sets of data will be examined, as shown in table of FIG. 6.

Simulation Results

Based on the data available provided in FIG. 6, two experiments were performed:

Experiment 1: Over-complete case: in this case, a complete sample data (see column 4 in FIG. 6) is used as input to the network and the output size is 2, as two original sources recovered.

Experiment 2: Squared case: this is a straight forward case with 2 inputs and 2 outputs when the data was rearranged so that each input is from the same sensor with non-overlapped consecutive sampling times ($t+i*\Delta t$ and $t+(i+1)*\Delta t$).

Experiment 1

In this case, the four subsets of the sampled data in FIG. 6 are studied and all data vectors available are used (the maximum number of data vectors is 12), which is less than the number of sensors (16).

Data Set 1

For data set 1, there are 12 mixtures of chemicals 1 and 7 and the data are shown in FIG. 7A.

FIG. 7B shows the separated signal sources 1 702 and 7 704 via space-invariant ICA of 12 inputs. FIG. 7C shows the original chemical sources 1 706 and 7 708 by averaging techniques.

Using the space-invariant ICA approach, the recovered signal sources (chemical 1 and 7 sources) are shown in FIG. 7B and the average of the single chemical source 1 and 7 are shown in FIG. 7C.

The spectrum of signal 702 in FIG. 7B is most closely matched to the signal 706 in FIG. 7C. Similarly the spectrum of signal 704 in FIG. 7B is most closely matched to the signal 708 in FIG. 7C.

To confirm its performance, the separated sources 1 and 7 were projected by ICA technique on the known 11 chemical sources shown in FIG. 5, the results are provided in the table in FIG. 8.

As can be inferred from FIG. 8, the single source of chemical 1 has the greatest overlap with the separated source, labeled separated chemical 1. Similarly, single source chemical 7 has the greatest overlap with separated chemical 7 from the mixture shown in FIG. 7A.

Data Set 2

Figure 9A:
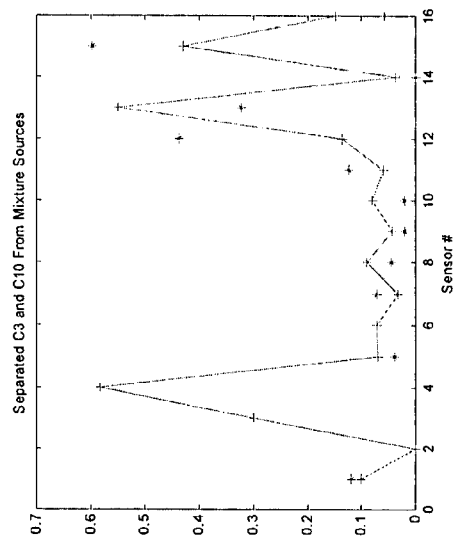
FIG. 9A is a graphical representation of 12 mixtures of chemicals 3 and 10 used in Experiment 1.

Data set 2, a mixture of chemicals 3 and 10, is plotted in FIG. 9A below.

Figure 9B:
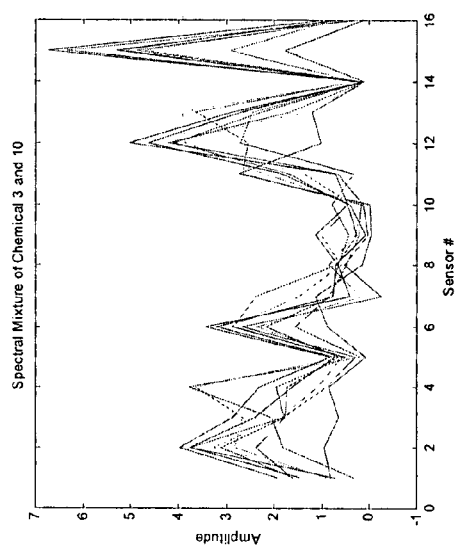
FIG. 9B is a graphical representation of separated signal sources of chemicals 3 and 10 by space-invariant ICA of 12 inputs.
Figure 9C:
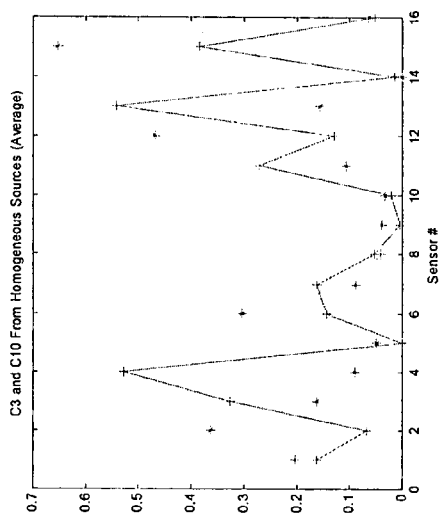
FIG. 9C is a graphical representation of the average of the single chemical source 3 and 10.

For the mixture from data set 2, the performance of space-invariant ICA has demonstrated its effective capability to separate the mixture of chemicals 3 and 10 as shown in FIG. 9B as compared with the original sources in FIG. 9C.

Table IV in FIG. 10 clearly indicates that the maximum sensor value in the column for separated chemical 3 was for chemical 3 while the maximum sensor value in the separated chemical 10 column was for chemical 10.

Data Set 3

Figure 11B:
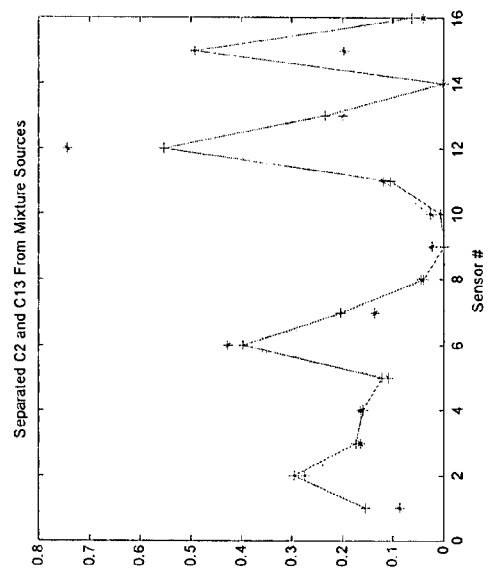
FIG. 11B is a graphical representation of separated signal sources of chemicals 2 and 13 by space-invariant ICA of 12 inputs.
Figure 11A:
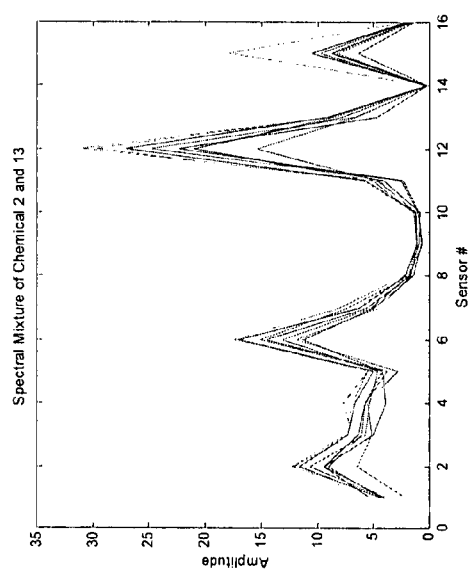
FIG. 11A is a graphical representation of 12 mixtures of chemicals 2 and 13 used in Experiment 1.

Data set 3, a mixture of chemicals 2 and 13, is plotted in FIG. 11A.

Figure 11C:
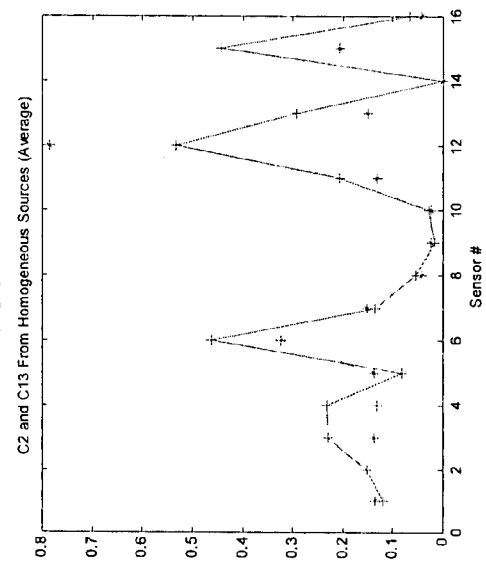
FIG. 11C is a graphical representation of the average of the single chemical source 2 and 13.

For the mixture of chemicals 2 and 13, space-invariant ICA has demonstrated its capability to separate the mixture of chemical 2 and 13 as shown in FIG. 11B as compared with the original sources in FIG. 11C.

FIG. 12 also clearly indicates that the separated chemical with the highest sensor value was chemical 2 among the separated chemical 2 data while chemical 13 captured the highest value among the data for separated chemical 13.

Data Set 4

Figure 13B:
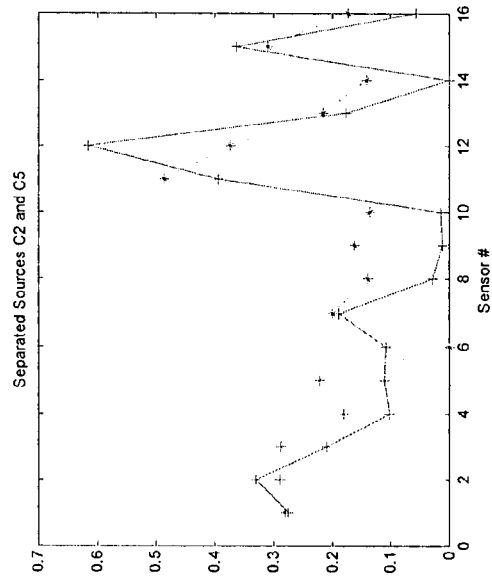
FIG. 13B is a graphical representation of separated signal sources of chemicals 2 and 5 by space-invariant ICA of 12 inputs.
Figure 13A:
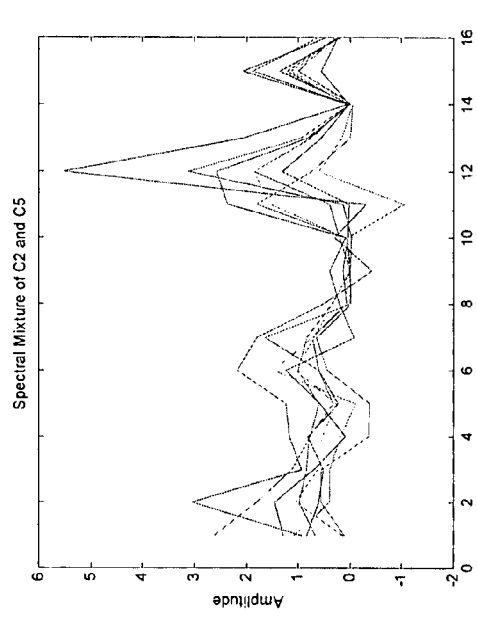
FIG. 13A is a graphical representation of 12 mixtures of chemicals 2 and 5 used in Experiment 1.

Data set 4, a mixture of chemicals 2 and 5, is plotted in FIG. 13A.

Figure 13C:
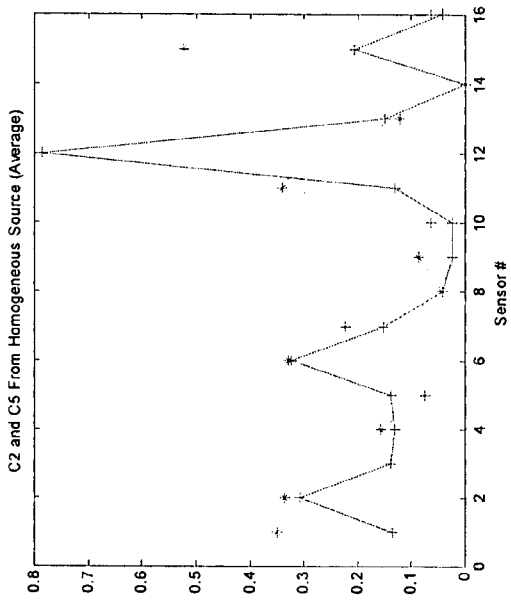
FIG. 13C is a graphical representation of the average of the single chemical source 2 and 5.

For mixture from data set 4 shown in FIG. 13A, space-invariant ICA has confirmed its powerful capability to separate the mixture of chemicals 2 and 5 as shown in FIG. 13B as compared with the original sources in FIG. 13C.

Table VI of FIG. 14 shows the correlation between the original and separated source of chemical 2 and 5.

Experiment 2

In this experiment, data set 1 (16×12) is paired in columns to obtain the data set 96×2. From this conversion, data values in a single row are the data from the same sensor with consecutive sampling times ($t+i*\Delta t$ and $t+(i+1)*\Delta t$); this new data set allows the same number of mixing sources and of original sources.

Using this new data set, space-invariant ICA has produced the results that were validated with the 11 known chemicals. Classification was 100% correct, based on the projection on 11 classes shown in FIG. 5.

To simplify the results, the mean and standard deviation of its projection were tabulated (separated sources of chemical 1 and chemical 7) on each single chemical source, and the results are summarized in the table in FIG. 15.

FIG. 15 is compact information to show that the separation sources from the mixture have successfully identified the original chemical sources.

Appendix A, incorporated herein by reference, further includes a series of flow chart diagrams providing the order in which data is processed and analyzed in the space-invariant independent component analysis.

Discussion

To separate two (2) mixing sources from a sixteen (16) element sensory data array, known as the over-complete case, poses a challenges for mathematical model and network topology. The non-overlapped paire-wise (i.e. sensor i and sensor i+1) or overlapped pair-wise (i.e. sensor i and sensor i+1) and (sensor i+1 and sensor i+2) so on) may face cumbersome and ineffective techniques.

As shown above, the mathematical model has demonstrated space-invariant ICA to be an effective topology to overcome insufficient data samples and the over-complete case. Moreover, the chemical data itself is fuzzy and inconsistent. The simulation demonstrated that the chemical source separation problem can be solved effectively with complete time sampling data (k=12) (under complete case) and two consecutive sampling data (k=2). Optimal topology may require a model of noise in order to determine the size of the sampling input. Moreover, space-invariant ICA governed by equation (4) is only valid when the sampling time is sufficiently small. Hence, the sampling time also plays an important role to ensure that the model approach holds.

Conclusions

A successful mathematical model to enable the space-invariant ICA topology from which Infomax and natural gradient descent technique can be applied has been demonstrated, and simulation has confirmed that the modeling is effective and sufficient to perform chemical source separation to enable the smart ENose to detect mixtures of chemicals in an open environment.

What is claimed is:

1. A computer implemented method for detection of chemicals in an open environment, the method comprising an act of causing a computer to perform operations of:

obtaining sampled data from a database containing data of air samples of an unknown open environment, the database created using a sensor array containing a plurality of sensors to obtain the data of air samples over a plurality of time intervals;

sampling a subset of the sampled data with respect to time for each sensor, wherein each subset includes a plurality of elements;

calculating operating points of each subset of the sampled data as an averaged value of each subset of the sampled data;

linearizing each subset of the sampled data using the operating points by subtracting the averaged value from each element in each corresponding subset of the sampled data;

determining a data distribution corresponding to each linearized subset of the sampled data;

performing an independent component analysis (ICA) on each linearized subset of the sampled data by using the data distribution, wherein the ICA generates independent component vectors representing each subset of the sampled data;

sampling data of known chemical elements representing spectral vectors from a database containing the data of known chemical elements;

iteratively performing an act of projecting the independent component vectors representative of each subset of the sampled data onto the data of the known chemical elements, wherein the step of projecting further comprises the steps of:

finding correlation between the independent component vectors of each subset of the sampled data and the spectral vectors of the known chemical elements;

finding a maximum value of the correlation and a known chemical element corresponding to the maximum value;

creating a list of chemical elements detected on each subset of the sampled data, wherein a known chemical element corresponding to the maximum value is added to the list of chemical elements detected;

outputting the list of chemical elements detected on each subset of the sampled data.

* * * * *